(12) United States Patent
Iwamoto et al.

(10) Patent No.: US 7,264,701 B2
(45) Date of Patent: Sep. 4, 2007

(54) REFERENCE ELECTRODE WITH NON-BLOCKING LIQUID JUNCTION

(75) Inventors: Yasukazu Iwamoto, Kyoto (JP); Naomi Kitaoka, Kyoto (JP)

(73) Assignee: Horiba, Ltd., Kyoto (JP)

( * ) Notice: Subject to any disclaimer, the term of this patent is extended or adjusted under 35 U.S.C. 154(b) by 482 days.

(21) Appl. No.: 10/384,209

(22) Filed: Mar. 7, 2003

(65) Prior Publication Data

US 2003/0209435 A1   Nov. 13, 2003

(30) Foreign Application Priority Data

Mar. 8, 2002 (JP) ............................ 2002-064134

(51) Int. Cl.
*G01N 27/40* (2006.01)
(52) U.S. Cl. ...................... 204/435; 204/419
(58) Field of Classification Search ............... 204/435, 204/419
See application file for complete search history.

(56) References Cited

U.S. PATENT DOCUMENTS

| | | | |
|---|---|---|---|
| 3,793,176 A * | 2/1974 | Jerrold-Jones | 204/435 |
| 4,209,368 A * | 6/1980 | Coker et al. | 205/525 |
| 4,401,548 A * | 8/1983 | Brezinski | 204/435 |
| 4,891,124 A * | 1/1990 | Rigdon et al. | 204/435 |
| 5,034,113 A | 7/1991 | Iwamoto | |
| 5,071,537 A * | 12/1991 | Yamaguchi et al. | 204/414 |
| 5,302,274 A * | 4/1994 | Tomantschger et al. | 204/412 |
| 5,344,548 A * | 9/1994 | Alberti et al. | 204/424 |
| 5,470,453 A * | 11/1995 | Nipkow et al. | 204/435 |
| 6,232,485 B1 * | 5/2001 | Derbyshire et al. | 558/102 |
| 6,495,012 B1 * | 12/2002 | Fletcher et al. | 204/435 |

FOREIGN PATENT DOCUMENTS

| | | |
|---|---|---|
| DE | 33 05 962 | 2/1985 |
| JP | 02-107959 | 4/1990 |
| JP | 07-159367 | 6/1995 |

OTHER PUBLICATIONS

Derwent abstract for DE 33 05 962 C2, Aug. 1984.*
Certified translation of DE 33 05 962 C2, Aug. 1984.*
Wang Bingji et al., "Study of new inorganic ion exchangers. I. Synthesis and properties of zirconium vanadopyrophosphate", Engineering Information, Inc., New York, NY, Apr. 1, 1994, XP-002266515 abstract only.
Chokkaram S. et al., "Ion Exchange and Thermal Studies of Sulfate Ziconia", Journal of Colliod and Interface Science, Academic Press, New York, NY, vol. 165, No. 1, Jun. 1, 1994, pp. 160-168.
Wang Bingjl et al., Study of New Inorganic Ion Exchangers, I. Synthesis and Properties of Zirconium Vanadoyrophosphate, Engineering Information, Inc., New York, NY, Apr. 1, 1994, XP-002266515; Full English Traslation.

* cited by examiner

*Primary Examiner*—Kaj K. Olsen

(57) ABSTRACT

A reference electrode traps silver ions and chloro complex ions leaching to an internal filling solution so that the blocking of the liquid junction can be prevented. A silver/silver chloride electrode can be provided as an internal electrode in an internal filling solution; and a tube which houses, in order from top to bottom, the internal electrode, an inorganic cation exchanger for trapping silver ions and/or chloro complex ions from leaching from the internal electrode, and a ceramic member for preventing the diffusion of the silver ions and/or the chloro complex ions to the internal filling solution.

28 Claims, 4 Drawing Sheets

REFERENCE ELECTRODE WITH NON-BLOCKING LIQUID JUNCTION

BACKGROUND OF THE INVENTION

1. Field of the Invention

The present invention relates to a reference electrode having an internal electrode in an internal filling solution, and more particularly to improvements that avoid blocking of a liquid junction.

2. Description of Related Art

When a reference electrode such as a silver/silver chloride is in operation, soluble silver ions ($Ag^+$) can leach from the silver/silver chloride electrode; and dissolved chloro complex ions (such as $AgCl_2^-$) can be formed by the following reactions:

  (1)

  (2)

If such chloro complex ions meet a low chloride ion water at the liquid junction, a reaction can proceed in the direction from right to left according to each formula above and consequently AgCl (silver chloride) can precipitate at the junction.

Particularly, in any continuous operation at a high temperature of 60° C. or above, the silver ions ($Ag^+$) and the dissolved chloro complex ions (such as $AgCl_2^-$) may increase in concentration, and at a lowered temperature, they can form silver chloride, with which the liquid junction can be blocked. Specifically, in continuous operation at 100° C., the liquid junction can be blocked with silver chloride within several days. Interfering substances such as proteins, silver, mercury, and $H_2S$ contained in liquid analytes can also come through the liquid junction into the internal filling solution. In such a case, they can also cause a displacement of the internal electrode potential or react with the silver ions to form less soluble precipitates with which the liquid junction can be blocked.

Therefore, conventional techniques include periodically replacing the internal filling solution to prevent an increase in the content of the silver or chloro complex ions, and/or forcing the internal filling solution to leak so that intake of the liquid analyte can be prevented under pressure changes caused by thermal cycles.

However, the former conventional technique does not drastically eliminate the silver ion, a liquid junction-blocking factor, and the maintenance thereof is not so easy. The later conventional technique needs a complicated structure of the reference electrode that will cause an increase in cost, and is less effective in continuous operation.

The present invention has been made in light of the above-mentioned problems.

SUMMARY OF THE INVENTION

An object of the present invention is to provide a reference electrode that can trap the silver ions and the chloro complex ions from leaching into the internal filling solution so that any blocking of the liquid junction can be prevented.

A further object is to provide a reference electrode having an internal electrode, an internal filling liquid and an inorganic cation exchanger positioned between the internal electrode and the internal filing liquid to prevent diffusion of ions from the internal electrode to the internal filling liquid.

A still further object is to provide one or more porous ceramic members between the reference electrode and the internal filing liquid to block ions.

Another object is to provide a particulate inorganic cation exchanger as an additive to the internal filling fluid.

In order to achieve these objects, the reference electrode according to the present invention can include a silver/silver chloride electrode as an internal electrode provided in an internal filling solution; and a tube which houses, in order from top to bottom, the internal electrode, an inorganic cation exchanger for trapping silver ions and/or chloro complex ions leaching from the internal electrode, and a ceramic member for preventing the diffusion of the silver ions and/or the chloro complex ions to the internal filling solution, wherein the tube is immersed in the internal filling solution.

Specifically, for example, between the internal electrode and the inorganic cation exchanger, the tube may house another ceramic member for inhibiting the leaching of the silver ions and/or the chloro complex ions from the internal electrode to the inorganic cation exchanger.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the coin vending art to make and use the invention and sets forth the best modes contemplated by the inventors of carrying out their invention. Various modifications, however, will remain readily apparent to those skilled in the art, since the general principles of the present invention have been defined herein specifically to provide an improved reference electrode that addresses blockage of the liquid junction.

The present invention is now described in detail with references to the drawings.

Figure 1:
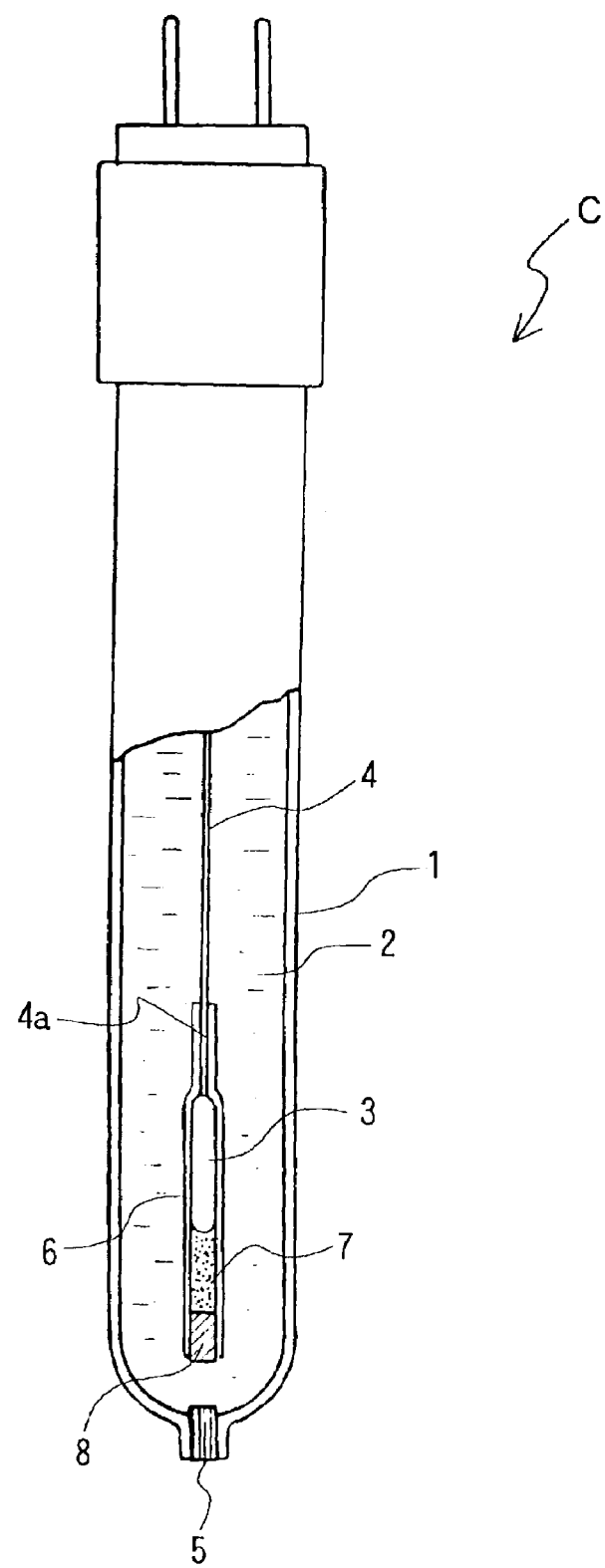
FIG. 1 is a partial view showing a structure of a first embodiment according to the present invention.

FIG. 1 shows a first embodiment according to the present invention including a tube which houses, in the order from top to bottom, an internal silver/silver chloride electrode, an inorganic cation exchanger, and a ceramic member, wherein the tube is immersed in an internal filling solution.

In FIG. 1, numeral 1 represents an outer tube of a reference electrode C, which is formed of a tube-shaped material such as glass tubing. Numeral 2 represents an internal filling solution such as a KCl solution charged in the outer tube 1. Numeral 3 represents an internal electrode such as a silver/silver chloride electrode having a part of a silver rod 4 and silver chloride which has been attached to a tip A of the silver rod in a fused state. The internal electrode 3 can be housed in an inner tube 6 as described below.

Numeral 5 represents a liquid junction that is provided at a lower end of the tube 1 and can be made of a material such as a ceramic. Examples of ceramic include ($SiO_2+Al_2O_3$) based ceramics and $ZrO_2$ based ceramics.

Numeral 6 represents an inner tube immersed in the internal filling solution 2. The inner tube 6 houses, in order from top to bottom, the internal silver/silver chloride electrode 3, an inorganic cation exchanger 7, and a ceramic member 8 for preventing the diffusion of silver ions ($Ag^+$) and chloro complex ions (such as $AgCl_2^-$) to the internal filling solution 2. The inorganic cation exchanger 7 has the function of trapping the silver ions ($Ag^+$) and the dissolved chloro complex ions (such as $AgCl_2^-$) that may leach from the internal electrode 3.

The ceramic member 8, which differs from the liquid junction 5 in material, has the function of preventing the diffusion of the silver ions ($Ag^+$) and the dissolved chloro complex ions (such as $AgCl_2^-$) from the internal electrode 3 to the internal filling solution 2. For example, the ceramic member 8 can be made of a porous ceramic preferably porous $Al_2O_3$ ceramic with a pore size of several μm to several tenths of μm.

For example, a $ZrO_2$ based cation exchanger manufactured by Toagosei Co., Ltd. as a particulate in a powder size within the range of 1 μm to 100 μm and distributed under the trade name IXE can be used as the inorganic cation exchanger 7.

In this embodiment, the inner tube 6 is formed of heat shrinkable tube preferably a polyolefine based heat-shrinkable tube. An adhesive is applied on the inner surface of the inner tube 6 so that in an upper place of the inner tube 6, a lower end portion 4a of the silver rod 4 and the internal electrode 3 extending therefrom in a lower direction are housed in a well-sealed manner. Preferred adhesives include polyimides.

In a lower place of the inner tube 6, the ceramic member 8 is also housed in a well-sealed manner.

In an intermediate place of the inner tube 6, the inorganic cation exchanger 7 is sandwiched between the internal electrode 3 at an upper position and the ceramic member 8 at a lower position and housed in a well sealed manner.

In this structure, the silver ions ($Ag^+$) and the dissolved chloro complex ions (such as $AgCl_2^-$) leaching from the internal electrode 3 are trapped by the inorganic cation exchanger 7 so that the generation of silver chloride can be prevented. The electrode potential can also be free from the influence which would otherwise be caused by deposition of silver chloride on the liquid junction 5. In addition, the ceramic member 8 when placed under the inorganic cation exchanger 7 can prevent the diffusion of the silver ions ($Ag^+$) and the dissolved chloro complex ions (such as $AgCl_2^-$) from migrating to the internal filling solution 2.

Figure 3:
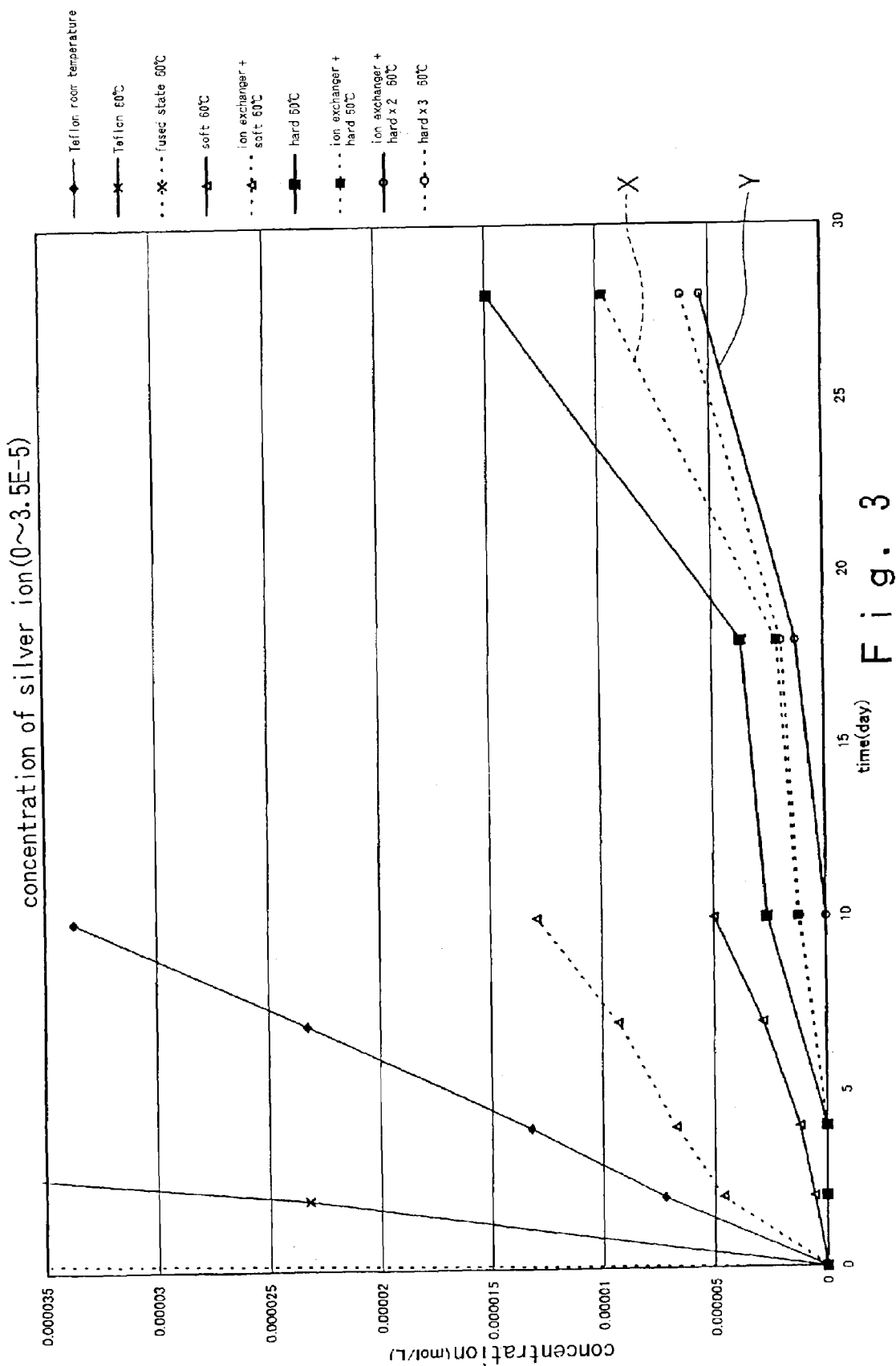
FIG. 3 is a chart diagram showing the effects of the present invention.

From a characteristic line indicated with X in FIG. 3, it can be understood that the generation of chloride ions in the liquid junction 5 is inhibited by the structure having the inorganic cation exchanger 7 at the lowermost part of the internal electrode 3 in contrast with those conventional examples each having only a Teflon (Registered trademark) coating on the internal silver chloride electrode. In FIG. 3, the ordinate axis represent the concentration of the silver ion in the internal filling solution 2.

Figure 2:
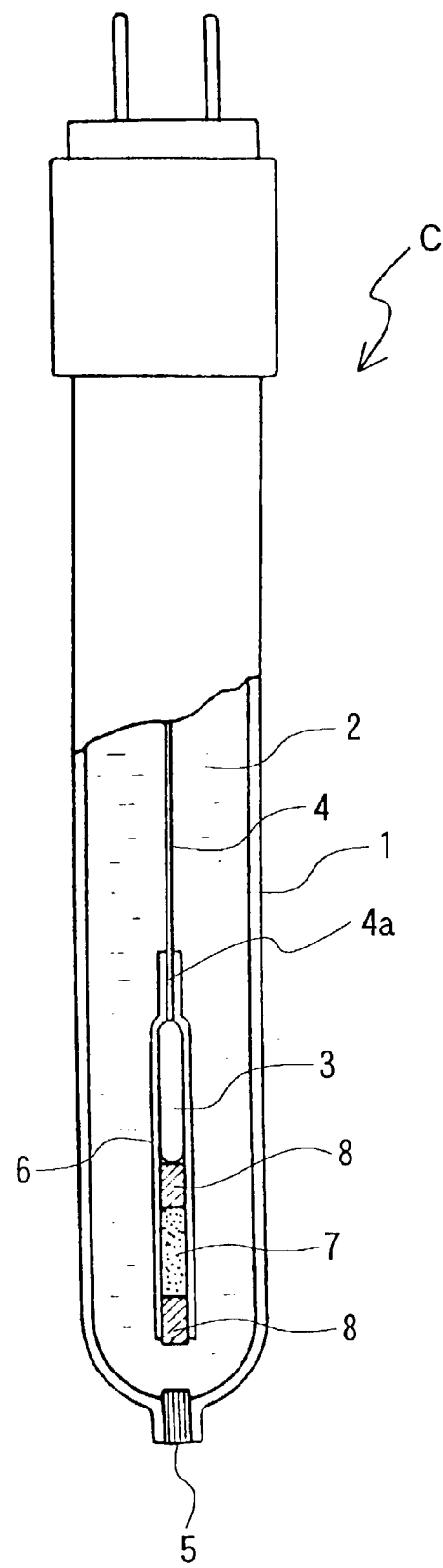
FIG. 2 is a partial view showing a structure of a second embodiment according to the present invention.

FIG. 2 shows a second embodiment according to the present invention including an inner tube 6 which houses, in order from top to bottom, an internal silver/silver chloride electrode 3; a ceramic member 8 for immediately blocking silver ions ($Ag^+$) and chloro complex ions (such as $AgCl_2^-$) leaching from the internal electrode 3 to an inorganic cation exchanger 7; the inorganic cation exchanger 7 for trapping the silver ions ($Ag^+$) and the dissolved chloro complex ions (such as $AgCl_2^-$) each leaching from the internal electrode 3; and a ceramic member 8 for preventing the diffusion of the silver ions ($Ag^+$) and the chloro complex ions (such as $AgCl_2^-$) from the internal electrode 3 to the internal filling solution 2, wherein the inner tube 6 is immersed in the internal filling solution 2. In FIGS. 1 and 2, the same numerals represent the same or corresponding elements.

In this embodiment, the inorganic cation exchanger 7 is sandwiched between the two ceramic members 8 and 8 placed at the upper and lower positions, respectively. In such a structure, the electrode potential can be more reliably freed from an influence which would otherwise be caused by deposition of silver chloride on the liquid junction 5.

The ceramic member 8 provided between the internal electrode 3 and the inorganic cation exchanger 7 prevents the dissolution (leaching) of the silver ions ($Ag^+$) and the dissolved chloro complex ions (such as $AgCl_2^-$) into the inorganic cation exchanger 7. Therefore, the ion exchange reaction by the inorganic cation exchanger 7 can be more effective in preventing the release of the ions to the internal filling solution 2.

From the characteristic line indicated with Y in FIG. 3, it can be further understood, that in contrast with the conventional examples each having only a Teflon coating on the internal silver/silver chloride electrode, the diffusion of the silver ions and the dissolved chloro complex ions to the internal filling solution 2 is more effectively suppressed by a structure having the inorganic cation exchanger 7 sandwiched between the two ceramic members 8 and 8, one provided at the lowermost part of the internal electrode 3 to immediately block the silver ions ($Ag^+$) and the dissolved chloro complex ions (such as $AgCl_2^-$) leaching to the inorganic cation exchanger 7, the other provided at the lowermost part of the inorganic cation exchanger 7 to have the function of preventing the diffusion of the silver ions ($Ag^+$) and the dissolved chloro complex ions (such as $AgCl_2^-$) from the internal electrode 3 to the internal filling solution 2.

Figure 4:
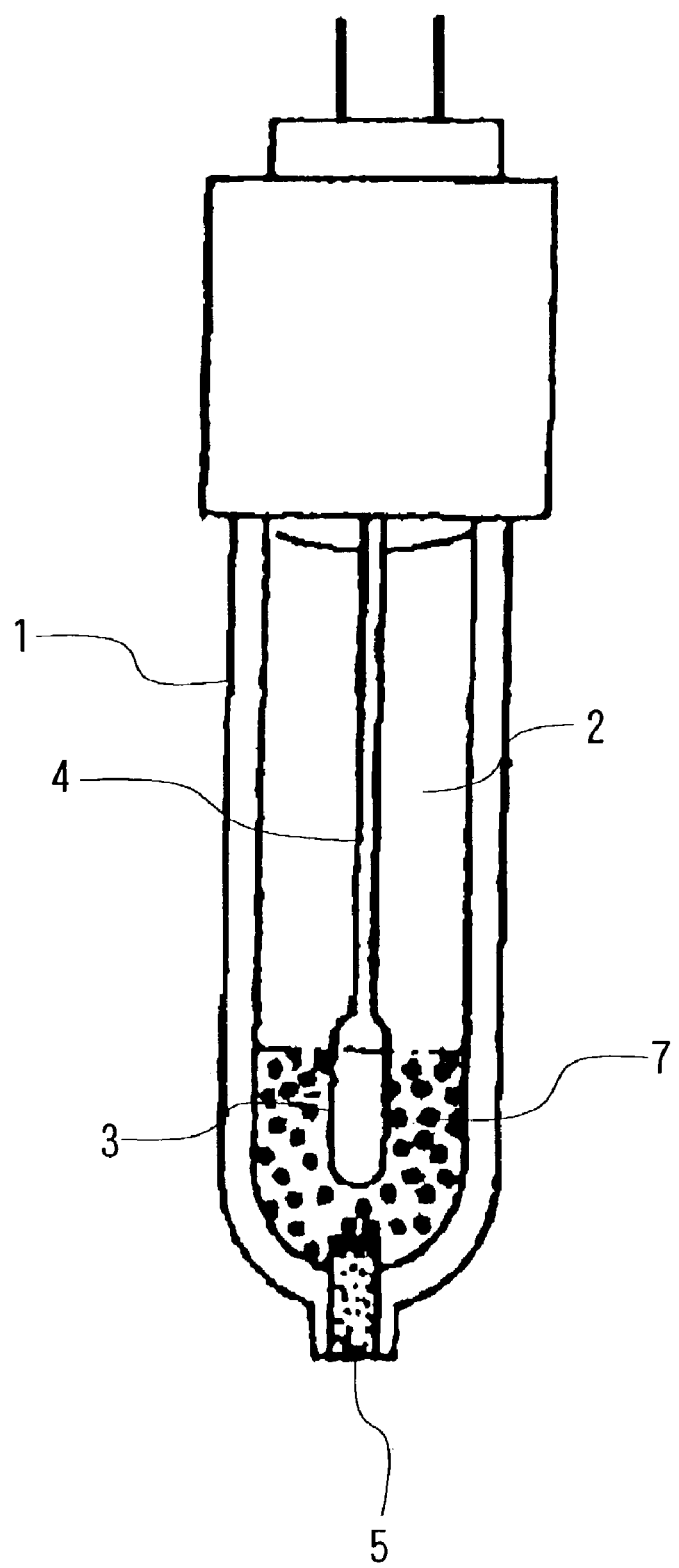
FIG. 4 is a schematic view showing a structure of a third embodiment according to the present invention.

FIG. 4 shows a third embodiment according to the present invention including an inorganic cation exchanger 7 which is provided in an internal filling solution 2 so as to trap silver ions ($Ag^+$) and dissolved chloro complex ions (such as such as $AgCl_2^-$) leaching from an internal electrode 3. In FIGS. 1 to 3, and 4, the same numerals represent the same or corresponding elements.

In this structure, the inorganic cation exchanger 7 is placed over the upper portion of a liquid junction 5. The inorganic cation exchanger 7 may be provided as a particulate additive to the internal filling solution 2 in the amount of 300 to 500 mg to a volume of internal fluid of 5 to 10 ml. The particulate cation exchanger 7 will settle to the bottom of the housing without being required to be fixed in place. This is particularly applicable to reference electrodes that are maintained in a static position.

This embodiment works as follows. As in the case of each embodiment described above, the inorganic cation exchanger 7 traps ions such as silver ions ($Ag^+$) so that the generation of silver chloride in the vicinity of the liquid junction 5 and the blocking thereof can effectively be prevented.

In addition, if the interfering substances such as proteins, silver, mercury, and $H_2S$ come through the liquid junction 5 into the internal filling solution 2, the inorganic cation exchanger 7 can scavenge them. Consequently, the displacement of the electrode potential which would otherwise be caused by the interfering substances can be avoided.

As described above, according to the present invention, the reference electrode includes an internal silver/silver chloride electrode provided in an internal filling solution; and a tube immersed in the internal filling solution, wherein the tube houses, in the order from top to bottom, the internal electrode, an inorganic cation exchanger for trapping silver ions and/or chloro complex ions leaching from the internal electrode, and a ceramic member for preventing the diffusion of the silver ions and/or the chloro complex ions to the internal filling solution.

Between the internal electrode and the inorganic cation exchanger, the tube may also have another ceramic member for blocking the silver ions and/or the chloro complex ions leaching from the internal electrode to the inorganic cation exchanger.

Accordingly, the silver ions and/or the chloro complex ions are trapped by the inorganic cation exchanger, and the diffusion of the silver ions and/or the chloro complex ions to the internal filling solution can immediately be suppressed, so that the generation of silver chloride can be prevented. In addition, the electrode potential can be free from the influence which would otherwise be caused by disposition of silver chloride on the liquid junction.

Those skilled in the art will appreciate that various adaptations and modifications of the just-described preferred embodiments can be reconfigured without departing from the scope and spirit of the invention. Therefore, it is to be understood that, within the scope of the appended claims, the invention may be practiced other than as specifically described herein.

What is claimed is:

1. In a reference electrode assembly having an internal electrode of a silver/silver chloride composition, immersed in an internal filling solution and a liquid junction, comprising a first portion and a second portion, the improvement comprising:
   an inner housing having a wall surrounding the internal electrode and sealed to the internal electrode at a first end of the inner housing via an adhesive applied to the first portion of the internal electrode and/or the wall surrounding the first portion of the internal electrode and open at a second end of the inner housing, wherein the inner housing is a heat shrinkable tube and the inner housing wall is immersed in the internal filling solution and blocks the internal filling solution egress to internal electrode to only the open second end of the inner housing;
   an inorganic cation exchanger material positioned adjacent the second portion of the internal electrode located at an edge of an end of the internal electrode within the inner housing such that the inorganic cation exchanger material only contacts the internal electrode at the second portion of the internal electrode whereby any dissolved silver ions and chloro complex-ions interacting with the inorganic cation exchanger material are trapped by the inorganic cation exchanger material; and
   a first porous ceramic member is sealed to the inner housing between the inorganic cation exchanger material and the second open end, the ceramic member has pore sizes for preventing diffusion of the silver ions and chloro complex-ions into the internal filling solution.

2. The reference electrode assembly of claim 1 wherein the inorganic cation exchanger material includes $ZrO_2$.

3. The reference electrode assembly of claim 2 wherein the porous ceramic member is $Al_2O_3$.

4. The reference electrode assembly of claim 3 wherein the pore sizes of the porous ceramic member is within a range of several μm to 0.1 μm.

5. The reference electrode assembly of claim 4 wherein the $ZrO_2$ is a particulate powder within a range of 1 μm to 100 μm in size.

6. The reference electrode assembly of claim 5 wherein the inner housing is a polyolefin heat-shrinkable tube and the adhesive is a polyimide based adhesive.

7. The reference electrode assembly of claim 6 has an internal filling solution of KCl.

8. The reference electrode assembly of claim 7 wherein the internal electrode has a rod of silver sealed to the first end of the inner housing and silver chloride is fused to the silver rod and is in contact with the $ZrO_2$.

9. The reference electrode assembly of claim 1 wherein the internal electrode is tightly sealed in the heat-shrinkable tube.

10. The reference electrode assembly of claim 1 wherein the adhesive is applied only to the first portion of the internal electrode and/or the wall surrounding the first portion of the internal electrode.

11. In a reference electrode assembly having an internal electrode of a silver/silver chloride composition, immersed in an internal filling solution and a liquid junction, comprising a first portion and a second portion, the improvement comprising:
    an inner housing having a wall surrounding the internal electrode and sealed to the internal electrode at a first end of the inner housing and open at a second end of the inner housing, the inner housing wall is immersed in the internal filling solution and blocks the internal filling solution egress to internal electrode to only the open second end of the inner housing;
    an inorganic cation exchanger material positioned within the inner housing whereby any dissolved silver ions and chloro complex-ions interacting with the inorganic cation exchanger material are trapped by the inorganic cation exchanger material;
    a first porous ceramic member is sealed to the inner housing adjacent the second open end, the ceramic member has pore sizes for preventing diffusion of the silver ions and chloro complex-ions into the internal filling solution; and
    a second porous ceramic member has a pore size for preventing diffusion of the silver ions and chloro complex-ions into the internal filling solution and is sealed to the inner housing and separates the inorganic cation exchanger material from the internal electrode.

12. The reference electrode assembly of claim 11 wherein the inorganic cation exchanger material includes $ZrO_2$.

13. The reference electrode assembly of claim 12 wherein at least one of the first or second porous ceramic member is $Al_2O_3$.

14. The reference electrode assembly of claim 13 wherein the pore sizes of at least one of the first or second porous ceramic member is within a range of several μm to 0.1 μm.

15. The reference electrode assembly of claim 14 wherein the $ZrO_2$ is a particulate powder within a range of 1 μm to 100 μm in size.

16. The reference electrode assembly of claim 15 wherein the inner housing is a polyolefin heat-shrinkable tube with a polyimide based adhesive sealing the tube at a first end to the internal electrode and at a second end to the porous ceramic member.

17. The reference electrode assembly of claim 16 has an internal filling solution of KCl.

18. The reference electrode assembly of claim 17 wherein the internal electrode has a rod of silver sealed to the first end of the inner housing and silver chloride is fused to the silver rod and is in contact with the $ZrO_2$.

19. A reference electrode assembly comprising;
an internal electrode of a silver/silver chloride composition comprising a first portion and a second portion;
the second portion of the internal electrode located at an edge of an end of the internal electrode;
an inner housing having a wall surrounding the internal electrode and sealed to the internal electrode at a first end of the inner housing via an adhesive applied to the first portion of the internal electrode and/or the wall surrounding the first portion of the internal electrode and open at a second end of the inner housing, wherein the inner housing is a polyolefin heat-shrinkable tube;
an internal filling solution surrounding the inner housing, the inner housing separating the internal electrode from the internal filling solution except at the open second end;
an inorganic cation exchanger material including $ZrO_2$ for interacting with any dissolved silver ions and chloro complex-ions to retard their introduction into the internal filling solution, wherein the inorganic cation exchanger is positioned adjacent the second portion of the internal electrode such that the inorganic cation exchanger material only contacts the internal electrode at the second portion of the internal electrode; and
a first porous member of $Al_2O_3$ having pore sizes for preventing diffusion of silver ions and chloro complex-ions into the internal filling solution, the inner housing is sealed to the first porous member to maintain the $ZrO_2$ between the first porous member and the internal electrode.

20. The reference electrode assembly of claim 19 wherein the pore size of the first porous member is within a range of several μm to 0.1 μm.

21. The reference electrode assembly of claim 20 further including a second porous member wherein the $ZrO_2$ is sandwiched between the first and second porous member within the inner housing.

22. The reference electrode assembly of claim 21 wherein the $ZrO_2$ is a particulate powder within a range of 1 μm to 100 μm in size.

23. The reference electrode assembly of claim 22 wherein the inner housing is a polyolefin heat-shrinkable tube and the adhesive is a polyimide based adhesive.

24. A reference electrode assembly comprising:
an outer housing having a liquid junction for interfacing with a sample;
an internal filling solution charged in the outer housing;
an internal electrode of a silver/silver chloride composition immersed in the internal filling solution in the outer housing comprising a first portion and a second portion;
the second portion of the internal electrode located at an edge of an end of the internal electrode;
an inner housing having a wall surrounding the internal electrode and sealed to the internal electrode at a first end of the inner housing via an adhesive applied to the first portion of the internal electrode and/or the wall surrounding the first portion of the internal electrode and the inner housing is open at a second end, the inner housing tubular wall prevents egress of any dissolved silver ions and chloro complex ions through the tubular wall into the internal filling liquid, wherein the inner housing is a heat-shrinkable tube;
an inorganic cation exchanger material including $ZrO_2$ for interacting with any dissolved silver ions and chloro complex-ions to retard their introduction into the internal filling solution along a length of the inner housing, wherein the inorganic cation exchanger is positioned adjacent the second portion of the internal electrode such that the inorganic cation exchanger material only contacts the internal electrode at the second portion of the internal electrode; and
a first porous member of $Al_2O_3$ having pore sizes for preventing diffusion of silver ions and chloro complex-ions into the internal filling solution, the inner housing tubular walls is sealed to the first porous member adjacent the open second end of the inner housing to maintain the $ZrO_2$ between the first porous member and the internal electrode.

25. The reference electrode assembly of claim 24 wherein the pore sizes of the first porous member is within a range of several μm to 0.1 μm.

26. The reference electrode assembly of claim 25 further including a second porous member within the $ZrO_2$ is sandwiched between the first and second porous members within the inner housing.

27. The reference electrode assembly of claim 26 wherein the $ZrO_2$ is a particulate powder within a range of 1 μm to 100 μm in size.

28. The reference electrode assembly of claim 27 wherein the inner housing is a polyolefin heat-shrinkable tube and the adhesive is a polyimide based adhesive.

* * * * *